United States Patent [19]

Kunz

[11] Patent Number: 5,049,569
[45] Date of Patent: Sep. 17, 1991

[54] METHOD FOR THE PROTECTION OF PLANTS AGAINST DISEASES

[75] Inventor: Walter Kunz, Oberwill, Switzerland

[73] Assignee: Ciba-Geigy Corporation, Ardsley, N.Y.

[21] Appl. No.: 325,848

[22] Filed: Mar. 20, 1989

[30] Foreign Application Priority Data

Mar. 25, 1988 [CH] Switzerland .................. 1141/88

[51] Int. Cl.$^5$ ............................................ A01N 43/40
[52] U.S. Cl. .................... 514/318; 514/183; 514/212; 514/227.8; 514/237.2; 514/252; 514/332; 514/336; 514/340; 514/342; 514/343; 514/354; 546/193; 546/323
[58] Field of Search ............... 546/193, 323; 514/318, 514/354, 183, 212, 227.8, 237.2, 252, 340, 343, 332, 342, 336

[56] References Cited

U.S. PATENT DOCUMENTS

| 4,092,421 | 5/1978 | Wade et al. | 514/354 |
| 4,148,902 | 4/1979 | Rigterink | 514/354 |
| 4,163,784 | 8/1979 | Holland | 514/227.8 |

FOREIGN PATENT DOCUMENTS 0614102 11/1979 Switzerland .

Primary Examiner—Mary C. Lee
Assistant Examiner—Jacqueline Haley
Attorney, Agent, or Firm—George R. Dohmann; Edward McC. Roberts

[57] ABSTRACT

Novel acylated urea derivatives of the general formula

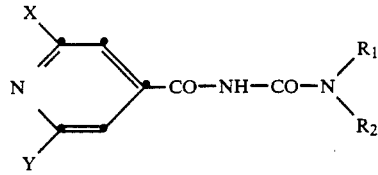

in which:

X is hydrogen or halogen; Y is halogen; $R_1$, $R_2$ independently of one another are hydrogen, $C_1$-$C_6$alkyl or $C_1$-$C_6$alkyl which is substituted by halogen, cyano, $C_1$-$C_4$alkoxy or COO-$C_1$-$C_3$alkyl, or is $C_3$-$C_5$alkenyl or $C_3$-$C_5$alkenyl which is substituted by halogen, or is $C_3$-$C_5$alkynyl or $C_3$-$C_5$alkynyl which is substituted by halogen, or is $C_3$-$C_7$cycloalkyl or $C_3$-$C_7$cycloalkyl which is substituted by $C_1$-$C_2$alkyl, halogen, cyano or COO-$C_1$-$C_3$alkyl, or is phenyl, benzyl or phenyl or benzyl which are substituted by $C_1$-$C_3$alkyl, $C_1$-$C_3$alkoxy or halogen; and $R_1$ can furthermore also be the radical Q or Q which is substituted by $C_1$-$C_3$alkyl, $C_3$-$C_7$cycloalkyl, $C_1$-$C_3$alkoxy or halogen, where Q can be bonded to the N atom via a $C_1$-$C_2$alkyl; or where $R_1$ and $R_2$ together with the adjacent N atom from a 3- to 7-membered heterocycle which can additionally contain 1 or 2 further hetero atoms such as O, N or S, and a carbonyl group and can be substituted by $C_1$-$C_3$alkyl, halogen or COO-$C_1$-$C_3$alkyl; Q is furan-2-yl, thiophen-2-yl, isoxazol-3-yl, isoxazol-3-yl, thiazol-2-yl, 1,2,4-thiadiazol-3-yl, 1,3,4-thiadiazol-2-yl, 2-, 3- or 4-pyridyl radicals or 2-, 3- or 4-pyridyl radicals which are substituted by $C_1$-$C_3$alkyl, $C_1$-$C_3$alkoxy, $C_1$-$C_3$alkylthio or halogen; 2-, 4- or 5-pyrimidyl radicals or 2-, 4- or 5-pyrimidyl radicals which are substituted by $C_1$-$C_3$alkyl, $C_1$-$C_3$alkoxy, $C_1$-$C_3$alkylthio, halogen or cyclopropyl.

The novel active substances have plant-protecting properties and are suitable in particular for the preventive protection of plants against infection with phytopathogenic microorganisms, such as fungi, bacteria and viruses.

7 Claims, No Drawings

METHOD FOR THE PROTECTION OF PLANTS AGAINST DISEASES

The present invention relates to novel acylated urea derivatives of the formula I below. The invention furthermore relates to the preparation of these substances, and to the agents containing at least one of these compounds as active substance. The invention moreover relates to the preparation of the agents mentioned, and to the use of the active substances or of the agents for the protection of plants against attack by microorganisms, for example, phytopathogenic fungi, bacteria and viruses.

The compounds according to the invention correspond to the general formula I

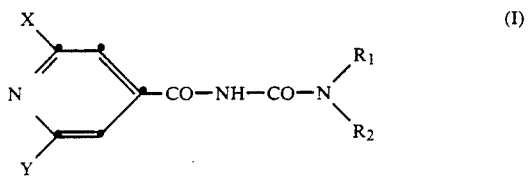

in which:

X is hydrogen or halogen; Y is halogen; $R_1$, $R_2$ independently of one another are hydrogen, $C_1$–$C_6$alkyl or $C_1$–$C_6$alkyl which is substituted by halogen, cyano, $C_1$–$C_4$alkoxy or COO-$C_1$–$C_3$alkyl, or is $C_3$–$C_5$alkenyl or $C_3$–$C_5$alkenyl which is substituted by halogen, or is $C_3$–$C_5$alkynyl or $C_3$–$C_5$alkynyl which is substituted by halogen, or is $C_3$–$C_7$cycloalkyl or $C_3$–$C_7$cycloalkyl which is substituted by $C_1$–$C_2$alkyl, halogen, cyano or COO-$C_1$–$C_3$alkyl, or is phenyl, benzyl or phenyl or benzyl which are substituted by $C_1$–$C_3$alkyl, $C_1$–$C_3$alkoxy or halogen; and $R_1$ can furthermore also be the radical Q or Q which is substituted by $C_1$–$C_3$alkyl, $C_3$–$C_7$-cycloalkyl, $C_1$–$C_3$alkoxy or halogen, where Q can be bonded to the N atom via a $C_1$–$C_2$alkyl; or where $R_1$ and $R_2$ together with the adjacent N atom form a 3- to 7-membered heterocycle which can additionally contain 1 or 2 further heteroatoms such as O, N or S, and a carbonyl group and can be substituted by $C_1$–$C_3$alkyl, halogen or COO-$C_1$–$C_3$alkyl; Q is furan-2-yl, thiophen-2-yl, isoxazol-3-yl, isoxazol-5-yl, thiazol-2-yl, 1,2,4-thiadiazol-3-yl, 1,3,4-thiadiazol-2-yl, 2-, 3- or 4-pyridyl radicals or 2-, 3- or 4-pyridyl radicals which are substituted by $C_1$–$C_3$alkyl, $C_1$–$C_3$alkoxy, $C_1$–$C_3$alkylthio or halogen; 2-, 4- or 5-pyrimidyl radicals or 2-, 4- or 5-pyrimidyl radicals which are substituted by $C_1$–$C_3$alkyl, $C_1$–$C_3$alkoxy, $C_1$–$C_3$alkylthio, halogen or cyclopropyl.

Halogen is fluorine, chlorine, bromine or iodine, preferably chlorine and further in the sequence bromine, fluorine and iodine. Halogen as substituent in the individual radicals can be present 1- to 3-fold.

Alkyl as such or as a constituent of another substituent is to be understood as meaning straight-chain and branched alkyls. Depending on the number of carbon atoms indicated, they are for example the following groups: methyl, ethyl and isomers of propyl, butyl, pentyl or hexyl, for example isopropyl, isobutyl, tertbutyl, sec-butyl or isopentyl.

Alkenyl is for example propen-1-yl, allyl, buten-1-yl, buten-2-yl or buten-3-yl, and alkynyl is for example propyn-2-yl, butyn-1-yl or pentyn-4-yl.

Cycloalkyl is chosen from amongst cyclopropyl, cyclobutyl, cyclopentyl, cyclohexyl or cycloheptyl, preferably cyclopropyl, cyclopentyl or cyclohexyl.

The invention particularly relates to compounds of the formula I in which:

X is hydrogen or halogen; Y is halogen; $R_1$, $R_2$ independently of one another are hydrogen, $C_1$–$C_6$alkyl or $C_1$–$C_6$alkyl which is substituted by halogen, cyano or COOC$_1$–$C_3$alkyl, or is $C_3$–$C_5$alkenyl or $C_3$–$C_5$alkenyl which is substituted by halogen, or is $C_3$–$C_5$alkynyl or $C_3$–$C_5$alkynyl which is substituted by halogen, or is $C_3$–$C_7$cycloalkyl or $C_3$–$C_7$cycloalkyl which is substituted by $C_1$–$C_2$alkyl, halogen, cyano or COO-$C_1$–$C_3$alkyl, or is benzyl or benzyl which is substituted by $C_1$–$C_3$alkyl, $C_1$–$C_3$alkoxy or halogen; and $R_1$ can furthermore also be the radical Q or Q which is substituted by $C_1$–$C_3$alkyl, $C_3$–$C_7$cycloalkyl, $C_1$–$C_3$alkoxy or halogen, where Q can be bonded to the N atom via a $C_1$–$C_2$alkyl; or where $R_1$ and $R_2$ together with the adjacent N atom form a 3- to 7-membered heterocycle, which can additionally contain 1 or 2 further heteroatoms, such as O, N or S, and a carbonyl group and can be substituted by $C_1$–$C_3$alkyl, halogen or COO-$C_1$–$C_3$alkyl; Q is furan-2-yl, isoxazol-3-yl, isoxazol-5-yl, thiazol-2-yl, 1,2,4-thiadiazol-3-yl, 1,3,4-thiadiazol-2-yl, 2-, 3- or 4-pyridyl radicals, or 2-, 3- or 4-pyridyl radicals which are substituted by $C_1$–$C_3$alkyl, $C_1$–$C_3$alkoxy, $C_1$–$C_3$alkylthio or halogen; 2-, 4- or 5-pyrimidyl radicals or 2-, 4- or 5-pyrimidyl radicals which are substituted by $C_1$–$C_3$alkyl, $C_1$–$C_3$alkoxy, $C_1$–$C_3$alkylthio, halogen or cyclopropyl.

By virtue of their particular plant-protecting properties, the compounds of the formula I can be divided into the following groups:

1. Compounds of the formula I in which:

X is hydrogen, fluorine, chlorine or bromine; Y is fluorine, chlorine or bromine; $R_1$ is $C_1$–$C_6$alkyl or $C_1$–$C_6$alkyl which is substituted by fluorine, chlorine, cyano or COOC$_1$–$C_3$alkyl, or is $C_3$–$C_5$alkenyl or $C_3$–$C_5$alkenyl which is substituted by chlorine, or is $C_3$–$C_5$alkynyl or $C_3$–$C_5$alkynyl which is substituted by chlorine, or is $C_3$–$C_7$cycloalkyl or $C_3$–$C_7$cycloalkyl which is substituted by COO-$C_1$–$C_3$alkoxy, or is benzyl or benzyl which is substituted by $C_1$–$C_3$alkoxy or halogen, or is Q; $R_2$ is hydrogen, $C_1$–$C_6$alkyl or $C_1$–$C_6$alkyl which is substituted by fluorine, chlorine, cyano or COO-$C_1$–$C_3$alkyl; $R_1$ and $R_2$ together with the adjacent N atom form a 4- to 7-membered heterocycle which can additionally contain a further N atom or an O atom and can be substituted by methyl or COO-$C_1$–$C_3$alkyl; Q is furan-2-yl, thiophen-2-yl, isoxazol-3-yl or isoxazol-5-yl, 2-, 3- or 4-pyridyl radicals or 2-, 3- or 4-pyridyl radicals which are substituted by $C_1$–$C_3$alkyl, $C_1$–$C_3$alkoxy or halogen; 2-, 4- or 5-pyrimidyl radicals or 2-, 4- or 5-pyrimidyl radicals which are substituted by $C_1$–$C_3$alkyl, $C_1$–$C_3$alkoxy or halogen.

2. Compounds of the formula I in which:

X is hydrogen, fluorine, chlorine or bromine; Y is fluorine, chlorine or bromine; $R_1$ is $C_1$–$C_6$alkyl or $C_1$–$C_6$alkyl which is substituted by halogen, or is Q; $R_2$ is hydrogen, $C_1$–$C_6$alkyl or $C_1$–$C_6$alkyl which is substituted by fluorine, chlorine, cyano or COO-$C_1$–$C_3$alkyl; $R_1$ and $R_2$ together with the adjacent N atom form a 4- to 7-membered heterocycle which can additionally contain an N- or an O-atom and can be substituted by halogen; Q is thiazol-2-yl, 1,2,4-thiazol-3-yl, 1,3,4-thiadiazol-2-yl, 2-, 3- or 4-pyridyl radicals or 2-, 3- or 4-pyridyl radicals which are substituted by $C_1$–$C_3$alkyl, $C_1$–$C_3$alkoxy or halogen.

Preferred sub-groups from the abovementioned groups of compounds are the following:

1.1 Compounds of the formula I in which:

X is hydrogen, chlorine or bromine; Y is chlorine or bromine; $R_1$ is $C_1$–$C_4$alkyl or $C_1$–$C_4$alkyl which is substituted by chlorine or COO-$C_1$–$C_3$-alkyl, or is $C_3$–$C_5$alkenyl, $C_3$–$C_5$alkynyl, cyclopropyl or cyclopropyl which is substituted by COOCH$_3$ or is benzyl or benzyl which is substituted by methoxy or chlorine, or is Q; $R_2$ is hydrogen, $C_1$–$C_4$alkyl or $C_1$–$C_4$alkyl which is substituted by chlorine or COO-$C_1$–$C_3$alkyl; $R_1$ and $R_2$ together with the adjacent N atom for a 5- or 6-membered heterocycle which can additionally contain a further N or an O atom and can be substituted by methyl or COO-$C_1$–$C_3$alkyl; Q is furan-2-yl, thiophen-2-yl, isoxazol-3-yl, isoxazol-5-yl, 2-, 3- or 4-pyridyl radicals or 2-, 3- or 4-pyridyl radicals which are substituted by $C_1$–$C_3$alkyl, $C_1$–$C_3$alkoxy, chlorine or bromine; 2-, 4- or 5-pyrimidyl radicals or 2-, 4- or 5-pyrimidyl radicals which are substituted by $C_1$–$C_3$alkyl, $C_1$–$C_3$alkoxy, chlorine or bromine.

2.1 Compounds of the formula I in which:

X is hydrogen, chlorine or bromine; Y is chlorine or bromine; $R_1$ is $C_1$–$C_4$alkyl or $C_1$–$C_4$alkyl which is substituted by fluorine or chlorine, or is Q; $R_2$ is hydrogen, $C_1$–$C_4$alkyl or $C_1$–$C_4$alkyl which is substituted by chlorine or COO-$C_1$–$C_3$alkyl; $R_1$ and $R_2$ together with the adjacent N atom form a 5-or 6-membered heterocycle which can additionally contain a further N atom or an O atom and can be substituted by chlorine or bromine; Q is thiazol-2-yl, 1,2,4-thiadiazol-3-yl, 1,3,4-thiadiazol-2-yl, 2-, 3- or 4-pyridyl radicals or 2-, 3- or 4-pyridyl radicals which are substituted by methyl, methoxy, fluorine, chlorine or bromine.

The following compounds are distinguished by particularly advantageous plant-protecting properties:
N-(2,6-Dichloroisonicotinoyl)carbamoylpiperidine;
N,N-Dimethyl-N'-(2,6-dichloroisonicotinoyl)urea.

Substituted acylated urea derivatives have already been disclosed, for example phenylaminocarbonylpyridine carboxamides are described as insecticides in U.S. Pat. No. 4,148,902.

Surprisingly, it has now been found that the compounds of the formula I according to the invention, when applied, inhibit the infection of plants by noxious microorganisms and therefore prevent damage to the plants caused by infection. It is characteristic for the active substances according to the invention that protection of the plants can result both by the direct action of the plant-pathogenic microorganisms by means of application via the leaf (direct action) or the soil (systemic action) and by activation and stimulation of the defense system of the plant (immunization). The large advantage of the compounds of the formula I is that maintenance of good health of the plants treated with these substances can also be ensured by itself without the application of other microbicidal substances during the vegetation period. Hence it is possible, by the application of the active substances according to the invention, to avoid disadvantageous side-effects, as may occur on direct control of parasites using chemical substances, for example on the one hand by damaging the crop plants (phytotoxicity) and on the other hand by causing resistance phenomena in the noxious microorganisms, and this advantageously results in an entirely undisturbed growth of the crop plants.

Due to the double mode of action of the compounds of the formula I according to the invention, i.e. on the one hand the direct control of the plant pathogens and on the other hand the increase of the general readiness for the challenge of the plants treated with these active substances by means of immunization, it is possible to achieve broad-range protection of the plants against diseases. The application of the active substances according to the invention is therefore particularly suitable for conditions in practice. Moreover, the systemic activity pertaining to the compounds of the formula I causes the protective effect to also extend to parts of the treated plants, which show additional growth.

The general plant-protecting activity of the active substances according to the invention is effective for example against the phytopathogenic fungi belonging to the following classes: *Fungi imperfecti* (for example Botrytis, Helminthosporium, Fusarium, Septoria, Cercospora and Alternaria); Basidiomycetes (for example the genera Hemileia, Rhizoctonia, Puccinia); Ascomycetes (for example Venturia, Podosphaera, Erysiphe, Monilinia, Uncinula).

Moreover, the active substances can be employed with particularly good success against the following noxious organisms: Fungi, for example Oomycetes (for example *Plasmopara viticola*, *Phytophthora infestans*, *Peronospora tabacina*, Pseudoperonospora), *Fungi imperfecti* (for example *Colletotrichum lagenarium*, *Pyricularia oryzae*, *Cercospora nicotinae*), Ascomycetes (for example *Venturia inaequalis*); bacteria, for example Pseudomonadaceae (*Pseudomonas lachrymans*, *Pseudomonas tomato*, *Pseudomonas tabaci*); Xanthomonadaceae (for example *Xanthomonas oryzae*, *Xanthomonas vesicatoria*); Erwinia (for example *Erwinia amylovora*); and viruses, for example tobacco mosaic virus.

The compounds according to the invention can be employed for the protection of various crop plants.

For example, the following plant species are suitable within the scope of the invention for the application of the compounds of the formula I according to the invention: cereals (wheat, barley, rye, oats, rice, sorghum and related species); beet (sugar beet and fodder beet); pomaceous fruit, stone fruit and soft fruit (apples, pears, plums, peaches, almonds, cherries, strawberries, raspberries and blackberries); pulses (beans, lentils, peas, soya beans); oil crops (oilseed rape, mustard, poppies, olives, sunflowers, coconuts, castor, cocoa, peanuts); cucurbits (pumpkins, cucumbers, melons); fibre plants (cotton, flax, hemp, jute); citrus fruit (oranges, lemons, grapefruit, tangerines); various vegetables (spinach, lettuce, asparagus, cabbage species, carrots, onions, tomatoes, potatoes, paprika); Lauraceae (avocado, Cinnamonum, camphor) or plants such as maize, tobacco, nuts, coffee, sugar cane, tea, vines, hops, banana plants and rubber plants, and also decorative plants (flowers, shrubs, deciduous trees and coniferous trees, such as conifers). This list is not intended to impose any restrictions.

Particularly suitable target crops for the application of the process according to the invention are the following plants: cucumber, tobacco, grape vines, rice, pepper, potatoes, tomatoes, wheat, barley, pears and apples.

The compounds of the formula I are prepared by reacting:

1. an isonicotinamide of the formula II

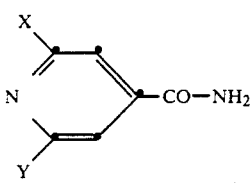  (II)

with
a) a carbamoyl halide of the formula IIIa

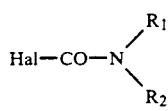  (IIIa)

or
b) a carbamoyl azolide of the formula IIIb

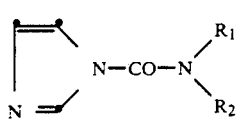  (IIIb)

or, for the preparation of those compounds of the formula I in which $R_1$ or $R_2$ is hydrogen,
c) with an isocyanate of the formula IIIc $$O=C=N-A \quad \text{(IIIc)}$$

in the presence of a base in aprotic solvents, where Hal in the abovementioned compounds is halogen, preferably chlorine, A is as defined for $R_1$ and $R_2$, and this radical and X and Y are as defined under formula I.

The reactions of process variants 1a, 1b and 1c take place at temperatures from 0° to 180° C.

Suitable bases are organic and inorganic bases, for example tertiary amines, such as trialkylamines (trimethylamine, triethylamine, tripropylamine etc.), pyridine, pyridine bases (4-dimethylaminopyridine, 4-pyrrolidylaminopyridine, collidine), oxides and hydroxides, carbonates and hydrogen carbonates of alkali metals and alkaline earth metals, and also alkali metal acetates.

Reaction media which are used depending on the specific reaction conditions are suitable solvents and diluents which are inert in the reaction. Examples which may be mentioned are: aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ether-like compounds, such as dialkyl ethers (dekthyl ether, diisopropyl ether, test-butyl methyl ether etc.), anisole, dioxane, tatrahydrofuran; nitriles, such as acetonitrile, propionitrile; N,N-dialkylated amides such as dimethylformamide; ketones, such as acetone, diethyl ketone, methyl ethyl ketone; and also mixtures of such solvents with one another.

2. In a further process for the preparation of the compounds of the formula I, a compound of the formula II

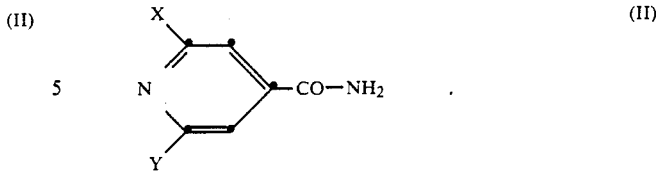  (II)

can be allowed to react
a) with $(COCl)_2$ or $CO(Cl)_2$ to give an isocyanate of the formula IV

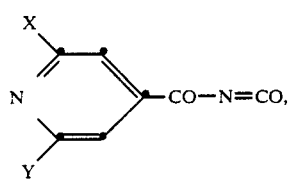  (IV)

which is then reacted
b) with an amine of the formula V

  (V)

the reaction according to 2a takes place at temperatures from −20° to 260° C. in inert solvents.

The subsequent reaction step according to 2b is carried out at temperatures from −40° to 100° C., preferably −10° to 50° C., preferably in the presence of catalytic amounts of a base, for example a tertiary amine, such as trimethylamine, triethylamine or diazabicyclooctane, in inert solvents.

Suitable reaction media for reaction steps 2a and 2b are, for example, the following solvents: ethers, such as diethyl ether, diisopropyl ether, tetrahydrofuran or dioxane, halogenated hydrocarbons, such as ethylene chloride, methylene chloride, trichloroethane, chloroform, and hydrocarbons, such as toluene or xylene.

The preparation of the starting materials is familiar to persons skilled in the art, and known from the literature.

For example, the amides of the formula II can be prepared by reacting an isonicotinic acid ester, isonicotinyl halide or isonicotinic acid azolide with ammonia in a solvent such as water, tetrahydrofuran, toluene, acetonitrile or a mixture thereof.

The abovementioned esters and halides are known or can be prepared by known methods (cf. Houben-Weyl 5/3, 925). The azolides are prepared for example either by reacting isonicotinyl halides with azoles or by reacting isonicotinic acid with dicarbonyldiimidazole (cf. Agnew. Chemie 1962, 409–411).

an advantageous process for the preparation of isonicotinamides of the formula II is the reaction of the acid halide with hexamethyldisilazane of the formula $[(CH_3)_2Si]_2NH$ or an analogous silylamine in an inert solvent, such as dichloromethane or trichloroethane, at temperatures from −10° to 80° C., preferably 0° to 40° C. and subsequent hydrolysis, for example using an alcohol, such as methanol, and dilute mineral acid, for example sulfuric acid (cf. Synthetic Communications 1985, 519).

The microbicidal agents for the protection of plants against diseases, which are applied within the scope of the invention and which contain the compounds of the formula I as active ingredients, form part of the invention.

Active substances of the formula I are customarily used in the form of compositions, and can be applied to the plant or its environment simultaneously or successively with other active substances. These other active substances can be fertilizers, suppliers of trace elements, or other preparations which influence plant growth. They can also be selective herbicides, insecticides, fungicides, bactericides, nematicides, molluscicides or mixtures of plurality of these preparations, and may be present together with other carriers, surfactants or application-facilitating additives conventionally used in the art of formulation.

Suitable carriers and additives can be solid or liquid and are substances which are expedient in the art of formulation, for example natural or regenerated mineral substances, solvents, dispersing agents, wetting agents, tackifiers, thickeners, binders or fertilizers.

One method for applying an active substance of the formula I or an agrochemical containing at least one of these active substances is application onto the plant (leaf application). However, the active substances of the formula I can also enter the plant via the soil through the root system (soil application) by watering the location of the plant with a liquid preparation, or by applying the substances to the soil in solid form, for example in the form of granules. However, the compounds of the formula I can also be applied to seeds (coating) either by soaking the grains in a liquid preparation of the active substance or by coating them with a solid preparation (application by seed dressing). Moreover, other ways of application are possible in specific cases, for example treatment of just the stems of the plants or the buds.

In this connection, the compounds of the formula I are employed as such or preferably together with the auxiliaries conventionally used in the art of formulation. For this purpose, they are processed in a known manner, for example to emulsion concentrates, spreadable pastes, solutions which can be sprayed directly or which can be diluted, dilute emulsions, wettable powders, soluble powders, dusts, granules, encapsulations in for example polymeric substances. The application methods such as spraying, atomizing, dusting, scattering, brushing-on or watering, like the type of agent, are chosen to suit the aims and the given circumstances. In general, advantageous application rates are 50 to 5 kg of active substance (AS) per ha; preferably 100 g to 2 kg of AS/ha, in particular 100 g to 600 g of AS/ha.

The formulations, i.e. the agents, preparations or compositions containing the active substance of the formula I and if desired a solid or liquid additive, are prepared by intimately mixing and/or grinding the active substances with extenders, for example with solvents, solid carriers, and if desired surface-active compounds (surfactants).

Suitable solvents are: aromatic hydrocarbons, preferably the fractions $C_8$ to $C_{12}$, for example xylene mixtures or substituted naphthalenes, phthalic acid esters, such as dibutyl or dioctyl phthalate, aliphatic hydrocarbons, such as cyclohexane or paraffins, alcohols and glycols as well as their ethers and esters, such as ethanol, ethylene glycol, ethylene glycol monomethyl ether or ethyl ether, ketones, such as cyclohexanone, strongly polar solvents, such as N-methyl-2-pyrrolidone, dimethyl sulfoxide or dimethylformamide; and epoxidized and non-epoxidized vegetable oils, such as epoxidized coconut oil or soya oil; or water.

Solid carriers which are customarily used, for example for dusts and dispersible powders, are natural ground minerals, such as calcite, talc, kaolin, montmorillonite or attapulgite. In order to improve the physical properties, it is also possible to add highly-disperse silica or highly-disperse absorbent polymers. Suitable adsorptive granulate carriers in the form of granules are porous types, for example pumice, brick grit, sepiolite or bentonite, as non-sorptive carrier materials for example calcite or sand. Moreover, a large number of pre-granulated materials of inorganic or organic origin, such as in particular dolomite or comminuted plant residues, can be used.

Possible surface-active compounds are non-ionic, cation- and/or anion-active surfactants having good emulsifying, dispersing and wetting properties, depending on the type of the active substance of the formula I to be formulated. Surfactants are also to be understood as meaning mixtures of surfactants.

Cationic surfactants are mainly quaternary ammonium salts which contain at least one alkyl radical having 8 to 22 C atoms as N-substituent and lower, halogenated or non-halogenated alkyl, benzyl or lower hydroxyalkyl radicals as other substituents.

Suitable anionic surfactants can be socalled water-soluble soaps and also water-soluble synthetic surface-active compounds.

Soaps which may be mentioned are the alkali metal salts, alkaline earth metal salts or substituted or unsubstituted ammonium salts of higher fatty acids ($C_{10}$–$C_{22}$), for example the Na or K salts of oleic or stearic acid or of natural mixtures of fatty acids which can be obtained for example from coconut oil or tallow oil.

Synthetic surfactants which can be used are in particular fatty alcohol sulfonates, fatty alcohol sulfates, sulfonated benzimidazole derivatives or alkyl sulfonates. The fatty alcohol sulfonates or fatty alcohol sulfates are usually in the form of alkali metal salts, alkaline earth metal salts or substituted or unsubstituted ammonium salts and have an alkali radical having 8 to 22 C atoms.

Suitable non-ionic surfactants are mainly polyglycol ether derivatives of aliphatic or cycloaliphatic alcohols, saturated or unsaturated fatty acids and alkylphenols and can contain 3 to 30 glycol ether groups and 8 to 20 carbon atoms in the (aliphatic) hydrocarbon radical and 6 to 18 carbon atoms in the alkyl radical of the alkylphenols.

The agents can also contain other additives, such as stabilizers, defoamers, viscosity regulators, binders, tackifiers and fertilizers or other active substances for achieving specific effects.

The agrochemical preparations usually contain 0.1 to 99% by weight, in particular 0.1 to 95% by weight, of active substance of the formula I, 99.9 to 1% by weight, in particular 99.8 to 5% by weight, of a solid or liquid additive and 0 to 25% by weight, in particular 0.1 to 25% by weight, of a surfactant.

The examples below are intended to illustrate the invention in more detail without imposing any restrictions.

1. Preparation Examples

EXAMPLE 1.1 a) Preparation of 2,6-dichloroisonicotinamide (starting material)

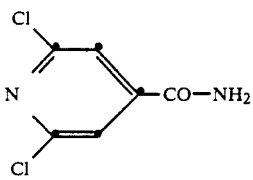

53.1 g of hexamethyldisilane are initially introduced into 600 ml of abs. methylene chloride. 63 g of 2,6-dichloroisonicotinyl chloride in 500 ml of methylene chloride are added dropwise and with cooling at 0°–5° C., and stirring is continued overnight at room temperature. On the next day, 60 ml of methanol and 600 ml of 5% sulfuric acid are added dropwise in succession. The precipitate which deposits is filtered off and washed with water. 54 g (95%) of white crystals of melting point 198–200° C. are obtained.

b) Preparation of 2,6-dichloroisonicotinoyl isocyanate (intermediate)

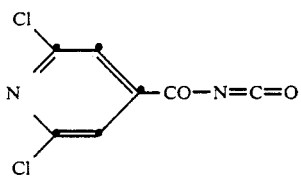

18 g of 2,6-dichloroisonicotinamide are dissolved in 180 ml of ethylene chloride, and 14.7 g of oxalyl chloride are added dropwise at 0°–5° C. The mixture is subsequently refluxed for 8 hours and cooled, and the solution is concentrated. Distillation under a high vacuum yields an oil boiling at 65°–7° C./4 Pa (82.1% of theory).

C) Preparation of N-(2,6-dichloroisonicotinoyl)carbamoylpiperidine (end product)

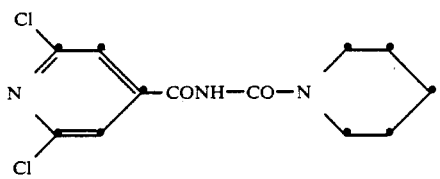

The solution of 1.51 g of the isocyanate obtained under a) in 5 ml of toluene are added dropwise at room temperature to 0.595 g of piperidine in 15 ml of abs. toluene. When the exothermic reaction has subsided, stirring is continued for 5 hours at room temperature, and the precipitate which has formed is subsequently filtered off. After recrystallization from acetone, white crystals of melting point 183°–185° C. are obtained.

The compounds listed below are prepared as described in the above preparation methods.

TABLE 1

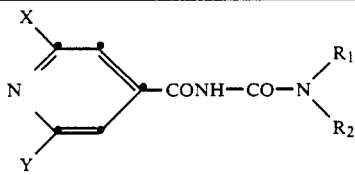

| Comp. No. | X | Y | $R_1$ | $R_2$ | Physical data |
|---|---|---|---|---|---|
| 1.1 | Cl | Cl | $CH_3$ | $CH_3$ | mp. 171–178° C. |
| 1.2 | Cl | Cl | $C_2H_5$ | $C_2H_5$ | mp. 135–137° C. |
| 1.3 | Cl | Cl | $C_3H_7(i)$ | $C_3H_7(i)$ | |
| 1.4 | Cl | Cl | $C_4H_9(n)$ | $C_4H_9(n)$ | mp. 81–84° C. |
| 1.5 | Cl | Cl | $C_4H_9(sec)$ | $C_4H_9(sec)$ | |
| 1.6 | Cl | Cl | H | $CH_3$ | mp. 264–266° C. |
| 1.7 | Cl | Cl | H | $C_3H_7(i)$ | |
| 1.8 | Cl | Cl | H | $C_4H_9(n)$ | mp. 149–150° C. |
| 1.9 | Cl | Cl | H | $C_4H_9(t)$ | mp. 191–193° C. |
| 1.10 | Cl | Cl | H | $C_6H_{13}(n)$ | |
| 1.11 | Cl | Cl | H | cyclopropyl | mp. 221–223° C. |
| 1.12 | Cl | Cl | H | cyclopentyl | mp. 181–184° C. |
| 1.13 | Cl | Cl | H | cyclohexyl | |
| 1.14 | Cl | Cl | H | $CH_2=CH-CH_2$ | |
| 1.15 | Cl | Cl | H | $CH_2C\equiv CH$ | |
| 1.16 | Cl | Cl | H | $CH_2CN$ | |
| 1.17 | Cl | Cl | H | $CH_2CH_2CN$ | |
| 1.18 | Cl | Cl | $CH_2CN$ | $CH_2CN$ | mp. 135–141° C. |
| 1.19 | Cl | Cl | $CH_2CH_2CN$ | $CH_2CH_2CN$ | mp. 165–166° C. |
| 1.20 | Cl | Cl | $-(CH_2)_5-$ | | mp. 183–185° C. |
| 1.21 | Cl | Cl | $-(CH_2)_4-$ | | |
| 1.22 | Cl | Cl | $-(CH_2)_2-CO-(CH_2)_2-$ | | |
| 1.23 | Cl | Cl | $-(CH_2)_6$ | | |
| 1.24 | Cl | Cl | $-(CH_2)O(CH_2)_2-$ | | mp. 195–198° C. |

TABLE 1-continued

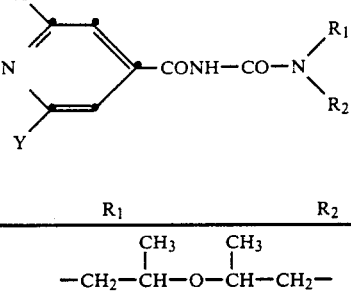

| Comp. No. | X | Y | R₁ | R₂ | Physical data |
|---|---|---|---|---|---|
| 1.25 | Cl | Cl | —CH₂—CH(CH₃)—O—CH(CH₃)—CH₂— | | mp. 200–202° C. |
| 1.26 | Cl | Cl | —CH₂—CH₂—S—CH₂—CH₂— | | |
| 1.27 | Cl | Cl | —CH₂—CH₂—N(CH₃)CH₂—CH₂— | | |
| 1.28 | Br | Br | —(CH₂)₅— | | |
| 1.29 | Br | Br | —(CH₂)₄— | | |
| 1.30 | Br | Br | —(CH₂)₇— | | |
| 1.31 | Br | Br | —CH₂—CH₂—O—CH₂—CH₂— | | |
| 1.32 | Cl | H | —(CH₂)₅— | | |
| 1.33 | Cl | H | —(CH₂)₄— | | |
| 1.34 | Cl | H | —(CH₂)₇— | | |
| 1.35 | F | F | —(CH₂)₅— | | |
| 1.36 | J | J | —(CH₂)₅— | | |
| 1.37 | Cl | H | —(CH₂)₅— | | |
| 1.38 | Cl | H | —(CH₂)₆— | | |
| 1.39 | Cl | H | cyclopropyl | H | |
| 1.40 | Cl | H | 1-(COOCH₃)-cyclopropyl | H | |
| 1.41 | Br | Br | CH₂—C≡CH | H | |
| 1.42 | Br | Br | CH₂—C≡CH₂ | H | |
| 1.43 | Br | Br | cyclohexyl | H | |
| 1.44 | Br | Br | cyclopropyl | H | |
| 1.45 | Br | Br | 1-(COOCH₃)-cyclohexyl | H | |
| 1.46 | Br | Br | CH₃ | CH₃ | |
| 1.47 | Br | Br | C₄H₉(sec) | C₄H₉(sec) | |
| 1.48 | Br | Br | benzyl | H | |
| 1.49 | Cl | H | 2-pyridyl | H | |
| 1.50 | F | F | 3-pyridyl | H | |
| 1.51 | F | F | 4-pyridyl | H | |
| 1.52 | Cl | Cl | benzyl | Me | |
| 1.53 | Cl | Cl | 2,6-(CH₃)₂—C₆H₃ | H | |
| 1.54 | Cl | Cl | 3,5-(Cl)₂—C₆H₃ | H | mp. 247–249° C. |
| 1.55 | Cl | Cl | 2-F—C₆H₄ | H | |
| 1.56 | Cl | Cl | 2-F-benzyl | H | |
| 1.57 | Cl | Cl | 4-Cl-benzyl | H | |
| 1.58 | Br | Br | C₄H₉(n) | C₄H₉(n) | |
| 1.59 | Br | Br | CH₂CH₂—CN | H | |
| 1.60 | F | F | CH₂—CN | CH₂CN | |
| 1.61 | F | F | CH₂—CN | H | |
| 1.62 | Cl | Cl | 2-Cl—C₆H₄ | H | mp. 244–247° C. |
| 1.63 | Cl | Cl | pyrimidinyl | H | |
| 1.64 | Br | Br | pyridyl | H | |

TABLE 1-continued
| Comp. No. | X | Y | R₁ | R₂ | Physical data |
|---|---|---|---|---|---|
| 1.65 | Cl | Cl | 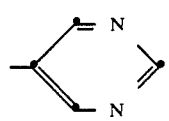 | H | mp. 205-207° C. |
| 1.66 | Cl | Cl | 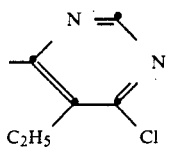 | H | |
| 1.67 | Cl | Cl | 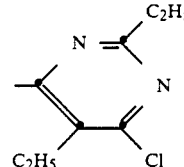 | H | mp. 177-179° C. |
| 1.68 | Cl | Cl | 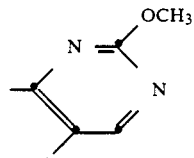 | H | |
| 1.69 | Cl | Cl | 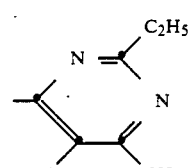 | H | |
| 1.70 | Cl | Cl | 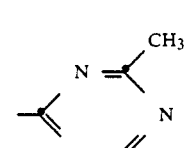 | H | |
| 1.71 | Cl | Cl | 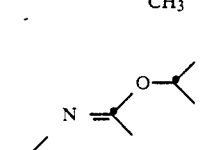 | H | |
| 1.72 | Cl | Cl |  | H | |

TABLE 1-continued
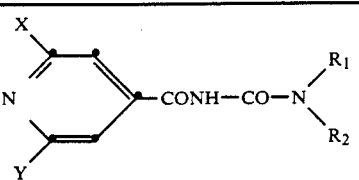
| Comp. No. | X | Y | R₁ | R₂ | Physical data |
|---|---|---|---|---|---|
| 1.73 | Cl | Cl | 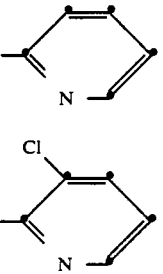 | CH₃ | |
| 1.74 | Cl | Cl | 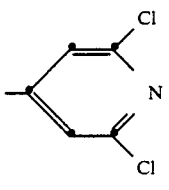 | H | |
| 1.75 | Cl | Cl | 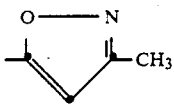 | H | |
| 1.76 | Cl | Cl | —CH(OC₂H₅)CN | H | |
| 1.77 | Cl | Cl | 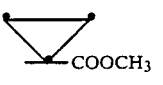 | H | mp. 180–182° C. |
| 1.78 | Cl | Cl | CH₂—CH═CH₂ | CH₂—CH═CH₂ | |
| 1.79 | Cl | Cl | CH₂C≡CJ | H | |
| 1.80 | Cl | Cl |  | H | |
| 1.81 | Cl | Cl | 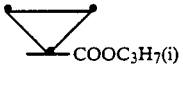 | H | |
| 1.82 | Cl | Cl |  | H | |
| 1.83 | Cl | Cl | 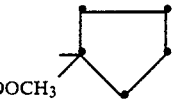 | H | |
| 1.84 | Cl | Cl | 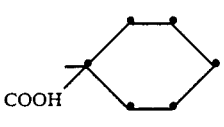 | H | |
| 1.85 | Cl | Cl |  | H | |
| 1.86 | Cl | Cl | cyclohexyl | H | |

TABLE 1-continued
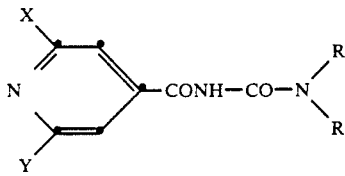
| Comp. No. | X | Y | R₁ | R₂ | Physical data |
|---|---|---|---|---|---|
| 1.87 | Cl | Cl |  | H | |
| 1.88 | Cl | Cl | cycloheptyl | H | |
| 1.89 | Cl | Cl | benzyl | H | mp. 215–217° C. |
| 1.90 | Cl | Cl | 1,2,4,-thiadiazol-3-yl | H | |
| 1.91 | Cl | Cl | 1,3,4,-thiadiazol-2-yl | H | mp. 250° C. (decomp.) |
| 1.92 | Cl | Cl | thiazol-2-yl | H | |
| 1.93 | Cl | Cl | 2-pyridyl | H | mp. 207–209° C. |
| 1.94 | Cl | Cl | 3-pyridyl | H | |
| 1.95 | Cl | Cl | 4-pyridyl | H | |
| 1.96 | Cl | Cl | 2-pyridyl | CH₃ | |
| 1.97 | Cl | Cl | thiophen-2-yl | CH₃ | |
| 1.98 | Cl | Cl | 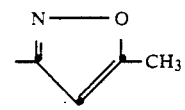 | H | mp. 193–195° C. |
| 1.99 | Br | Br | 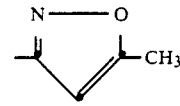 | H | |
| 1.100 | Cl | H | 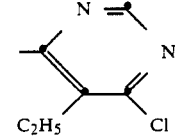 | H | |
| 1.101 | Br | Br | 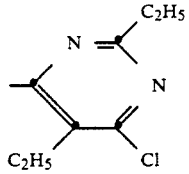 | H | |
| 1.102 | J | J | 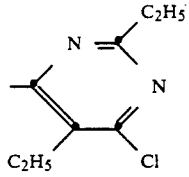 | H | |
| 1.103 | F | F | 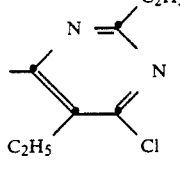 | H | |

TABLE 1-continued

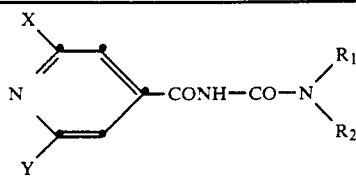

| Comp. No. | X | Y | $R_1$ | $R_2$ | Physical data |
|---|---|---|---|---|---|
| 1.104 | Cl | Cl | 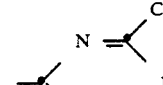 | $CH_3$ | |
| 1.105 | Cl | Cl | 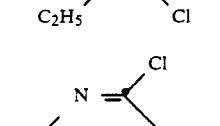 | H | |

TABLE 2

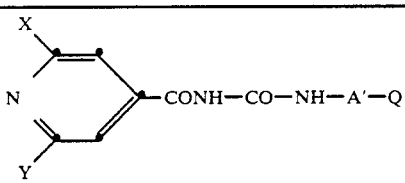

| Comp. No. | X | Y | A' | Q | Physical data |
|---|---|---|---|---|---|
| 2.1 | Cl | Cl | —$CH_2$— | 3-pyridyl | |
| 2.2 | Cl | H | —$CH_2$—$CH_2$— | 4-pyridyl | |
| 2.3 | Cl | Cl | —$CH_2$— | 2-furyl | mp. 188–189° C. |
| 2.4 | Cl | Cl | —$CH_2$— | 2-thienyl | mp. 188–190° C. |
| 2.5 | Cl | Cl | —$CH_2$— | 2-pyridyl | mp. 222–224° C. |
| 2.6 | Cl | Cl | —$CH_2$— | 4-pyridyl | |
| 2.7 | Cl | Cl | —$CH_2CH_2$— | 2-furyl | |
| 2.8 | Cl | Cl | —$CH(CH_3)$— | 2-furyl | |
| 2.9 | Br | Br | —$CH(CH_3)$— | 2-pyridyl | |
| 2.10 | F | F | —$CH_2$— | 2-furyl | |
| 2.11 | Cl | Cl | —$CH(CH_3)$— | 2-furyl | |

TABLE 3

(Intermediate of the formula IV)

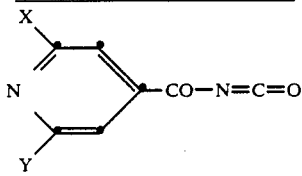

| Comp. No. | X | Y | Physical data |
|---|---|---|---|
| 3.1 | Cl | Cl | b.p. 65–67° C./4 Pa |
| 3.2 | Br | Br | |
| 3.3 | Cl | H | |
| 3.4 | F | F | |
| 3.5 | J | J | |

2. Formulation examples of active substances of the formula I (% is percent by weight)

| 2.1 Wettable powder | (a) | (b) | (c) |
|---|---|---|---|
| Active substance from the TABLES | 25% | 50% | 75% |
| Na ligninsulfonate | 5% | 5% | — |
| Na lauryl sulfate | 3% | — | 5% |
| Na diisobutylnaphthalenesulfonate | — | 6% | 10% |
| Octylphenol polyethylene glycol ether (7–8 mol of ethylene oxide) | — | 2% | — |
| Highly-disperse silica | 5% | 10% | 10% |
| Kaolin | 62% | 27% | — |

The active substance is mixed with the additives and ground to homogeneity in a suitable mill. Wettable powders which can be diluted with water to give suspensions of any desired concentration are obtained.

| 2.2 Emulsion cencentrate | |
|---|---|
| Active substance from the TABLES | 10% |
| Octylphenol polyethylene glycol ether (4–5 mol of ethylene oxide) | 3% |
| Ca dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| 2.3 Dusts | (a) | (b) |
|---|---|---|
| Active substance from the TABLES | 5% | 8% |
| Talc | 95% | — |
| Kaolin | — | 92% |

Ready-for-use dusts are obtained by mixing the active substance with the carriers and grinding the mixture in a suitable mill.

| 2.4 Extruder granules | |
| --- | --- |
| Active substance from the TABLES | 10% |
| Na ligninsulfonate | 2% |
| Carboxymethyl cellulose | 1% |
| Kaolin | 87% |

The active substance is mixed with the additives, and the mixture is ground and moistened with water. This mixture is extruded and subsequently dried in a stream of air.

| 2.5 Coated granules | |
| --- | --- |
| Active substance from the TABLES | 3% |
| Polyethylene glycol (MW 200) | 3% |
| Kaolin | 94% |

(MW = molecular weight)

The kaolin, which has been moistened with polyethylene glycol, is uniformly coated with the finely ground active substance in a mixer. In this manner, dust-free coated granules are obtained.

| 2.6 Suspension concentrate | |
| --- | --- |
| Active substance from the TABLES | 40% |
| Ethylene glycol | 10% |
| Nonylphenol polyethylene glycol ether (15 mol of ethylene oxide) | 6% |
| Na-ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is mixed intimately with the additives. A suspension concentrate is obtained which can be used for the preparation of suspensions of any desired concentration by dilution with water.

3. Biological examples

EXAMPLE 3.1

Action against *Colletotrichum lagenarium* on Cucumis sativus L a) After a 2-week growing period, cucumber plants are sprayed with a spray mixture prepared with a wettable powder of the active substance (concentration: 200 ppm). After 48 hours, the plants are inoculated with a spore suspension ($1.5 \times 10^5$ spores/ml) of the fungus and incubated at a high relative atmospheric humidity and a temperature of 23° C. for 35 hours. The incubation is then continued at normal atmospheric humidity and at 22° C. to 23° C.

The protective action is assessed 7-8 days after the inoculation, based on the infection with the fungus.

b) After a 2-week growing period, cucumber plants are treated with a spray mixture prepared from a wettable powder of the active substance, by soil application (concentration:60 or 20 ppm relative to the soil volume). After 48 hours, the plants are inoculated with the spore suspension ($1.5 \times 10^5$ spores/ml) of the fungus and incubated at a high relative atmospheric humidity and a temperature of 23° C. for 35 hours. The incubation is then continued at normal atmospheric humidity and at 22° C.

The protection action is assessed 7-8 days after the inoculation based on the infection with the fungus.

c) After a 2-week period, cucumber plants are sprayed with a spray mixture prepared from a wettable powder of the active substance (concentration: 200 ppm).

After 3 weeks, the plants are inoculated with spore suspension ($1.5 \times 10^5$ spores/ml) of the fungus and incubated at a high relative atmospheric humidity and a temperature of 23° C. for 36 hours. The incubation is then continued at normal atmospheric humidity and at 22° to 23° C.

The protective action is assessed 7-8 days after the inoculation based on the infection with the fungus.

Compounds from Tables 1 and 2 showed good effects in the tests. For example, the compound 1.1, 1.77 or 1.98 reduced infection with the fungus to 0 to 20%. In contrast, untreated but inoculated control plants showed an infection with Colletotrichum of 100%.

EXAMPLE 3.2

Action against *Puccinia graminis* on wheat a) 6 Days after sowing, wheat plants are sprayed with a spray mixture prepared from a wettable powder of the active substance (0.02% of active substance). After 24 hours, the treated plants are inoculated with a uredospore suspension of the fungus. The inoculated plants are incubated for 48 hours at 95-100% relative atmospheric humidity and approx. 20° C. and then placed in a greenhouse at approx. 22° C. The development of rust pustules is assessed 12 days after inoculation.

b) A spray mixture prepared from a wettable powder of the active substance is poured next to wheat plants 5 days after sowing (0.006% of active substance relative to the soil volume). After 48 hours, the treated plants are inoculated with a uredospore suspension of the fungus. The inoculated plants are incubated for 48 hours at 95-100% relative atmospheric humidity and approx. 20° C. and then placed in a greenhouse at approx. 22° C. The development of the rust pustules is assessed 12 days after the inoculation.

Compounds from Tables 1 and 2 showed good effects against Puccinia fungi. For example the compounds 1.1, 1.18, 1.24 and 1.25 reduced infection with the fungus to 0 to 20%. In contrast, untreated but inoculated control plants showed an infection with Puccinia of 100%.

EXAMPLE 3.3

Action against *Phytophthora infestans* on tomato plants a) After a 3-week growing period, tomato plants are sprayed with a spray mixture prepared with a wettable powder of the active substance (0.02% of active substance). After 24 hours, the treated plants are inoculated with a sporangia suspension of the fungus. The infection with the fungus was assessed after an incubation of inoculated plants for 5 days at 90-100% relative atmospheric humidity and 20° C.

b) After a 3-week growing period, a spray mixture prepared with a wettable powder of the active substance is poured next to tomato plants (0.006% of active substance relative to the soil volume). Contact of the spray mixture with the above-ground parts of the plants is avoided. After 48 hours, the treated plants are inoculated with a sporangia suspension of the fungus. The infection of the fungus is assessed after an incubation of the inoculated plants for 5 days at 90-100% relative atmospheric humidity and 20° C.

Compounds from Table 1 and 2 showed a good protective action against the Phytophthora fungus. For example, the compounds 1.1, 1.2, 1.11, 1.12, 1.24, 1.25, 1.77, 1.85, 1.89, 1.91 and 1.93 reduced infection with the fungus to 0 to 20%. In contrast, untreated but inoculated control plants showed an infection with Phytophthora of 100%.

EXAMPLE 3.4

Action against *Plasmopara viticola* on grapevines a) Grapevine seedlings in the 4-5 leaf stage are sprayed with a spray mixture prepared with a wettable powder of the active substance (0.02% of active substance). After 24 hours, the treated plants are inoculated with a sporangia suspension of the fungus. Infection with the fungus is assessed after an incubation for 6 days at 95-100% relative atmospheric humidity and 20° C.

b) Grapevine seedlings in the 4-5 leaf stage are inoculated with a sporangia suspension of the fungus. After an incubation for 24 hours in a humid chamber at 95-100% relative atmospheric humidity and 20° C., the inoculated plants are dried and sprayed with a spray mixture prepared with a wettable powder of the active substance (0.06% of active substance). After the spray coating has dried on, the treated plants are transferred back to the humid chamber. Infection with the fungus is assessed 6 days after the inoculation.

Compounds from Tables 1 and 2 showed a good protective action against *Plasmopara viticola* (0-20% infection), for example the compounds 1.4, 1.20 and 1.67. In contrast, untreated but inoculated control plants showed a 100% infection with Plasmopara.

EXAMPLE 3.5

Action against *Pyricularia oryzae* on rice plants a) After a 2-week growing period, rice plants are sprayed with a spray mixture prepared with a wettable powder of the active substance (0.02% of active substance). After 48 hours, the treated plants are inoculated with a conidia suspension of the fungus. Infection with the fungus is assessed after incubation for 5 days at 95-100% relative atmospheric humidity and 24° C.

b) A spray mixture prepared with a wettable powder of the active substance (0.006% of active substance relative to the soil volume) is poured next to 2-week old rice plants. The pots are then filled with water so that the lower parts of the stems of the rice plants are in the water. After 96 hours, the treated rice plants are inoculated with a conidia suspension of the fungus. Infection with the fungus is assessed after the infected plants have been incubated for 5 days at 95-100% relative atmospheric humidity and approx. 24° C.

Compared with untreated control plants (100% infection), rice plants which have been treated with a spray mixture containing a compound from Tables 1 and 2 as the active substance showed only little infection with the fungus. For example in test (a), the compounds 1.1, 1.2, 1.4, 1.6, 1.18, 1.19, 1.20, 1.65, 1.67, 1.77, 1.93, 1.98 and in test (b) the compounds 1.4, 1.6, 1.8, 1.9, 1.19, 1.20, 1.62, 1.65, 1.67, 1.77, 2.3, 2.4 and 2.5 reduced the infection to 0 to 20%.

EXAMPLE 3.6

Seed treatment against *Pyricularia oryzae* on rice plants 100 kg of dry "upland rice" are treated for approx. 1 hour in a mixer with a wettable powder (formulation WP-25) containing 200 g of A.S. until the surface of the rice grains is coated uniformly with the formulated active substance.

The rice seeds which have been prepared in this manner are sown in plots of size 10 m$^2$, the edges of which are planted with rice plants showing infection with *Pyricularia oryzae* (=leaf blast). After the rice seedlings have emerged, the first evaluation of infection is carried out as soon as the rice plants show spots on the leaves. More evaluations are then carried out in intervals of one week.

Compounds from Tables 1 and 2 showed good effects in the test. For example, the compound 1.12 or 1.20 reduced infection of the rice plants with Pyricularia to 0 to 20%. In contrast, control plants from untreated seeds showed infection with the disease of 100%.

EXAMPLE 3.7

Action against *Xanthomonas oryzae* on rice (*Oryza staiva*)

a) After a 3-week growing period in the greenhouse, rice plants cv. "Calora" or "S6" are sprayed with the test substance in form of a spray mixture (0.02% of active substance). After this spray coating had dried on for one day, the plants are placed in a growth chamber at 24° C. and 75-85% relative atmospheric humidity and inoculated. The inoculation is carried out by cutting off the leaf tips with a pair of scissors which have previously been dipped into a suspension of *Xanthomonas oryzae*. If infected, the leaves where the cuts were made wilt after incubation for 10 days, roll up and turn necrotic. The extent of these disease symptoms is used for assessing the residual effectiveness of the test substance.

b) After a 3-week growing period in the greenhouse, rice plants cv. "Calora" or "S6" are watered with a suspension of the test substance (0.006% of active substance relative to the soil volume). Three days after this treatment, the plants are placed in a growth chamber at 24° C. and 75-85% relative atmospheric humidity and inoculated. The inoculation is carried out by cutting off the leaf tips with a pair of scissors which have previously been dipped into a suspension of *Xanthomonas oryzae*. If infected, the leaves where the cuts were made wilt after incubation for 10 days, roll up and turn necrotic. The extend of these disease symptoms is used for assessing the systemic effectiveness of the test substance.

Compounds from Tables 1 and 2 showed a good protective action against *Xanthomonas oryzae*. For example, in test (a), the compounds 1.1, 1.6, 1.24 and 1.25 and, in test (b), compounds 1.1, 1.6, 1.18, 1.20, 1.24, 1.25 and 1.62 reduced infection with the bacteria to 0 to 20%. In contrast, untreated but inoculated control plants showed an infection with the disease of 100%.

EXAMPLE 3.8

Action against *Xanthomonas vesicatoria* on paprika (*Capsicum annuum*)

a) After a 3-week period in the greenhouse, paprika plants cv. "California Wonder" are sprayed with the test substance in the form of a spray mixture (0.02% of active substance). After this spray coating has dried on for one day, the plants are placed in a growth chamber at 25° C. and 95-100% relative atmospheric humidity and inoculated by spraying the undersides of the leaves with a standardized suspension of *Xanthomonas vesicatoria*. If infected, round, initially watery, later necrotic, pale spots occur on the leaves after 6 days of incubation.

The extent of these spots is used for assessing the residual effectiveness of the test substance.

b) After a 3-week growing period in the greenhouse, paprika plants cv. "California Wonder" are watered with a suspension of the test substance (0.006% of active substance relative to the soil volume). Three days after this treatment, the plants are placed in a growth chamber at 26° C. and 95-100% relative atmospheric humidity and inoculated by spraying the leaf undersides with a standardized suspension of *Xanthomonas vesicatoria*. If infected, round, initially watery, later necrotic, pale spots occur on the leaves after 6 days of incubation. The extent of these spots is used for assessing the systemic effectiveness of the test substance.

Compounds from Tables 1 and 2 showed a good protective action against *Xanthomonas vesicatoria*. For example, in Test (a), the compound 1.24 and in Test (b) the compounds 1.1, 1.20, 1.24, 1.25 and 1.62 reduced infection with bacteria to 0 to 20%. In contrast, untreated but inoculated control plants showed an infection with the disease of 100%.

EXAMPLE 3.9

Action against *Pseudomonas tomato* on tomato plants a) After a 3-week growing period, tomato plants are treated by leaf application with a spray mixture prepared with a wettable powder of the active substance (concentration: 200 ppm). After 3.5 weeks, the plants are inoculated with a bacteria suspension (108 bacteria/ml) and incubated for 6 days at high relative atmospheric humidity and at a temperature of 20° C. 7-8 days after inoculation, the protective action is assessed based on the infection with bacteria.

In this test, untreated but inoculated control plants show an infection rate of 100%.

Compounds from Tables 1 and 2 showed a good protective action against *Pseudomonas tomato*. For example, plants which had been treated for example with compound 1.20, 1.24 or 1.25 remained essentially free of Pseudomonas (infection rate: 20 to 0%).

b) After a 3-week growing period, tomato plants were treated by soil application with a spray mixture prepared with a wettable powder of the active substance (concentration: 60 ppm relative to the soil volume). After 3.5 weeks, the plants were inoculated with a bacteria suspension (108 bacteria/ml) and incubated for 6 days at high relative atmospheric humidity and at a temperature of 25° C.

7-8 days after inoculation, the protective action is assessed based on the infection with bacteria.

In this test, untreated but inoculated control plants show an infection rate of 100%.

Compounds from Tables 1 and 2 have a good effect against *Pseudomonas tomato*. For example, plants which had been treated for example with compound 1.1, 1.20, 1.24 or 1.25 remained virtually free of Pseudomonas (infection rate 20 to 0%).

EXAMPLE 3.10

Action against *Erysiphe graminis* on barley a) Barley plants of approx. height 8 cm are sprayed with a spray mixture prepared with a wettable powder of the active substance (0.02% of active substance). After 3-4 hours, the treated plants are dusted with conidia of the fungus. The inoculated barley plants are placed in a greenhouse at approx. 22° C., and infection with the fungus is assessed after 10 days.

b) A spray mixture prepared with a wettable powder of the active substance (0.006% of active substance relative to the soil volume) is poured next to barley plants of approx. height 8 cm. Contact of the spray mixture with the above-ground parts of the plants is avoided. After 48 hours, the treated plants are dusted with conidia of the fungus. The inoculated barley plants are placed in a greenhouse at approx. 22° C., and infection of the fungus is assessed after 10 days.

Compounds from Tables 1 and 2, for example compound 1.20, reduced infection with the fungus to less than 20%, while untreated but inoculated control plants showed an infection rate of 100%.

What is claimed is:

1. A method of protecting plants against infection by phytopathogenic microorganisms, which comprises applying an effective amount of an active compound to the plants or their locus, said active compound being a compound of the formula $$\text{(I)}$$

in which

X is hydrogen or halogen; Y is halogen; $R_1$, $R_2$ independently of one another are hydrogen, $C_1$-$C_6$alkyl or $C_1$-$C_6$alkyl which is substituted by halogen, cyano or $COOC_1C_3$alkyl, is $C_3$-$C_5$alkenyl or $C_3$-$C_5$alkenyl which is substituted by halogen, or is $C_3$-$C_5$alkynyl or $C_3$-$C_5$alkynyl which is substituted by halogen, or is $C_3$-$C_7$cycloalkyl or $C_3$-$C_7$cycloalkyl which is substituted by $C_1$-$C_2$alkyl, halogen, cyano or $COO$-$C_1$-$C_3$alkyl, is benzyl or benzyl which is substituted by $C_1$-$C_3$alkyl, $C_1$-$C_3$alkoxy or halogen; and $R_1$ can furthermore also be the radical Q or Q which is substituted by $C_1$-$C_3$alkyl, $C_3$-$C_7$cycloalkyl, $C_1$-$C_3$alkoxy or halogen, where Q can be bonded to the N atom via a $C_1$-$C_2$alkyl; or where $R_1$ and $R_2$ together with the adjacent atom form a 5- to 8-membered saturated heterocycle which can additionally contain 1 further heteroatom selected from the group consisting of O, N and S, and a carbonyl group, said heterocycle being unsubstituted or substituted by $C_1$-$C_3$alkyl, halogen or $COO$-$C_1$-$C_3$alkyl; Q is a furan-2-yl, thiophen-2-yl, isoxazol-3-yl, isoxazol-5-yl, thiazol-2-yl, 1,2,4-thiadiazol-3-yl, 1,3,4-thiadiazol-2-yl, 2-, 3- or 4-pyridyl radical or a 2-, 3- or 4-pyridyl radical which is substituted by $C_1$-$C_3$alkyl, $C_1$-$C_3$alkoxy, $C_1$-$C_3$alkylthio or halogen; a 2-, 4- or 5-pyrimidyl radical or a 2-, 4-or 5-pyrimidyl radical which is substituted by $C_1$-$C_3$alkyl, $C_1$-$C_3$alkyl, $C_1$-$C_3$alkoxy, $C_1$-$C_3$alkylthio, halogen or cyclopropyl.

2. A method according to claim 1 where:
X is hydrogen, fluorine, chlorine or bromine; Y is fluorine, chlorine or bromine; $R_1$ is $C_1$-$C_6$alkyl or $C_1$-$C_6$alkyl which is substituted by fluorine, chlorine, cyano or $COOC_1$-$C_3$alkyl, or is $C_3$-$C_5$alkenyl or $C_3$-$C_5$alkenyl which is substituted by chlorine, or is $C_3$-$C_5$alkynyl or $C_3$-$C_5$alkynyl which is substituted by chlorine, or is $C_3$-$C_7$cycloalkyl or $C_3$-$C_7$cycloalkyl which is substituted by COO- $C_1$-$C_3$alkoxy, or is benzyl or benzyl which is substituted by $C_1$-$C_3$alkoxy, or is benzyl or benzyl which is substituted by $C_1$-$C_3$alkoxy or halogen, or is Q; $R_2$ is hydrogen, $C_1$-$C_6$alkyl or $C_1$-$C_6$alkyl which is substituted by fluorine, chlorine cyano or COO-$C_1$-$C_3$alkyl; $R_1$ and $R_2$ together with the adjacent N atom form a 5- to 7-membered heterocycle which can additionally contain a further N atom or an O atom and can be substituted by methyl or COO-$C_1$-$C_3$alkyl; Q is furan-2-yl, thiophen-2-yl, isoxazol-3yl or isoxazol-5-yl, 2-, 3- or 4-pyridyl radicals or 2-, 3- or 4-pyridyl radicals which are substituted by $C_1$-$C_3$alkyl, $C_1$-$C_3$alkoxy or halogen; 2-, 4- or 5-pyrimidyl radicals or 2-, 4- or 5-pyrimidyl radicals which are substituted by $C_1$-$C_3$alkyl, $C_1$-$C_3$alkoxy or halogen.

3. A method according to claim 1, where:

X is hydrogen, fluorine, chlorine or bromine; Y is fluorine, chlorine or bromine; $R_1$ is $C_1$-$C_6$alkyl or $C_1$-$C_6$alkyl which is substituted by halogen, or is Q; $R_2$ is hydrogen, $C_1$-$C_6$alkyl or $C_1$-$C_6$alkyl which is substituted by fluorine, chlorine, cyano or COO-$C_1$-$C_3$alkyl; $R_1$ and $R_2$ together with the adjacent N atom form a 5- to 7-membered heterocycle which can additionally contain an N-or an O-atom and can be substituted by halogen; Q is thiazol-2-yl, 1,2,4-thiazol-3-yl, 1,3,4-thiadiazol-2-yl, 2-, 3- or 4-pyridyl radicals or 2-, 3- or 4-pyridyl radicals which are substituted by $C_1$-$C_3$alkyl, $C_1$-$C_3$alkoxy or halogen.

4. A method according to claim 2 where:

X is hydrogen, chlorine or bromine; Y is chlorine or bromine; $R_1$ is $C_1$-$C_4$alkyl or $C_1$-$C_4$alkyl which is substituted by chlorine or COO-$C_1$-$C_3$-alkyl, or is $C_3$-$C_5$alkenyl, $C_3$-$C_5$alkynyl, cyclopropyl or cyclopropyl which is substituted by COOCH$_3$, or is benzyl or benzyl which is substituted by methoxy or chlorine, or is Q; $R_2$ is hydrogen, $C_1$-$C_4$alkyl or $C_1$-$C_4$alkyl which is substituted by chlorine or COO-$C_1$-$C_3$alkyl; $R_1$ and $R_2$ together with the adjacent N atom for a 5- or 6-membered heterocycle which can additionally contain a further N or an O atom and can be substituted by methyl or COO-$C_1$-$C_3$alkyl; Q is furan-2-yl, thiophen-2-yl, isoxazol-3-yl, isoxazol-5-yl, 2-, 3-or 4-pyridyl radicals or 2-, 3- or 4-pyridyl radicals which are substituted by $C_1$-$C_3$alkyl, $C_1$-$C_3$alkoxy, chlorine or bromine; 2-, 4- 5-pyrimidyl radicals or 2-, 4- or 5-pyrimidyl radicals which are substituted by $C_1$-$C_3$alkyl, $C_1$-$C_3$alkoxy, chlorine or bromine.

5. A method according to claim 4, where:

X is hydrogen, chlorine or bromine; Y is chlorine or bromine; $R_1$ is $C_1$-$C_4$alkyl or $C_1$-$C_4$alkyl which is substituted by fluorine or chlorine, or is Q; $R_2$ is hydrogen, $C_1$-$C_4$alkyl or $C_1$-$C_4$alkyl which is substituted by chlorine or COO-$C_1$-$C_3$alkyl; $R_1$ and $R_2$ together with the adjacent N atom form a 5- or 6-membered heterocycle which can additionally contain a further N atom or an O atom and can be substituted by chlorine or bromine; Q is thiazol-2-yl, 1,2,4-thiadiazol-3-yl, 1,3,4-thiadiazol-2-yl, 2-, 3- or 4-pyridyl radicals or 2-, 3- or 4-pyridyl radicals which are substituted by methyl, methoxy, fluorine, chlorine or bromine.

6. A method of claim 1 wherein N-(2,6-dichloroisonicotinoyl)carbamoyl piperidine is the active compound.

7. A method of claim 1 wherein N,N-dimethyl-N'-(2,6-dichloroisonicotinoyl) urea is the active compound.

* * * * *